Figure 1:
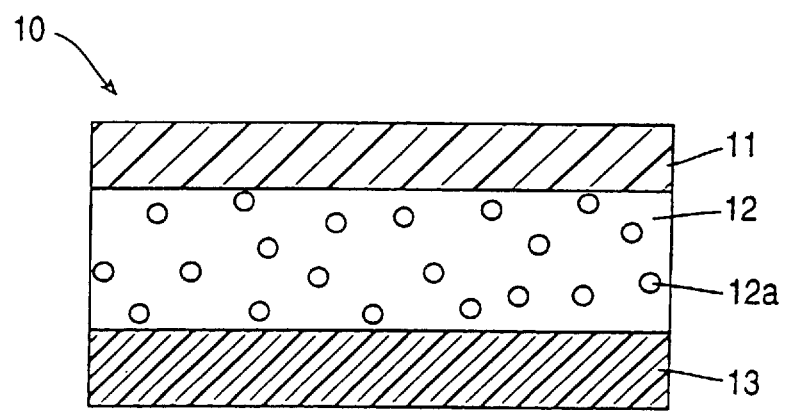

United States Patent [19]
Ma et al.

[11] Patent Number: 5,843,472
[45] Date of Patent: Dec. 1, 1998

[54] TRANSDERMAL DRUG DELIVERY SYTEM FOR THE ADMINISTRATION OF TAMSULOSIN, AND RELATED COMPOSITIONS AND METHODS OF USE

[75] Inventors: Xinghang Ma, Pleasanton; Jay Audett, Mountain View; Pravin L. Soni, Sunnyvale; Noel Singh, San Francisco; Susan E. Bailey, San Leandro, all of Calif.

[73] Assignee: Cygnus, Inc., Redwood City, Calif.

[21] Appl. No.: 807,448

[22] Filed: Feb. 28, 1997

[51] Int. Cl.$^6$ ...................................................... A61F 13/00
[52] U.S. Cl. .......................... 424/449; 424/448; 514/946; 514/947
[58] Field of Search ................... 424/448, 449; 514/946, 947

[56] References Cited

U.S. PATENT DOCUMENTS

| | | | |
|---|---|---|---|
| 4,915,950 | 4/1990 | Miranda | 424/448 |
| 5,116,615 | 5/1992 | Gokeen et al. | 424/94.2 |
| 5,232,702 | 8/1993 | Pfister | 424/448 |
| 5,447,958 | 9/1995 | Niigata et al. | 514/603 |
| 5,464,437 | 11/1995 | Reid et al. | 607/101 |
| 5,503,843 | 4/1996 | Santus et al. | 424/448 |
| 5,603,947 | 2/1997 | Wong | 424/448 |

FOREIGN PATENT DOCUMENTS 0 249 343    12/1987    European Pat. Off. .
0 760 238 A1    3/1997    European Pat. Off. .

OTHER PUBLICATIONS

Mitomi, M., et al., Chem. Abstracts, vol. 126, No. 1, 1997, #11538c, 1997.
Bostwick et al., (Feb. 3, 1992) "The Association of Bengin Prostatic Hyperplasia and Cancer of the Prostate," *Cancer* 70(Suppl 1):291–301.
"Benign Prostatic Hyperplasia," *Cecil Textbook of Medicine*, (1992) 19:1352–1353.
*Supplement to Urology*, (Dec. 1984) 24(6):1–16.
"Bacteriuria and Associated Infections of the Reproductive System in Men," *Urinary Tract Infection and Inflammation*, (1989):92–123.

*Primary Examiner*—D. Gabrielle Brouillette
*Attorney, Agent, or Firm*—Dianne E. Reed; Kenneth Barovsky Bozicevic & Reed LLP

[57] ABSTRACT

Drug delivery systems for the transdermal administration of tamsulosin are described. The systems are in the form of laminated patches having one or more reservoirs comprised of a polymeric adhesive material containing a tamsulosin formulation. The invention also relates to a method for treating benign prostatic hypertrophy (BPH) and related conditions and diseases, by administering tamsulosin transdermally, to tamsulosin-containing pharmaceutical compositions for transdermal administration of the drug and to a low-temperature method for manufacturing a tamsulosin-containing transdermal delivery system.

25 Claims, 11 Drawing Sheets

TRANSDERMAL DRUG DELIVERY SYTEM FOR THE ADMINISTRATION OF TAMSULOSIN, AND RELATED COMPOSITIONS AND METHODS OF USE

TECHNICAL FIELD

This invention relates generally to transdermal drug delivery, and more particularly relates to drug delivery systems for administering tamsulosin transdermally, to drug reservoirs contained in such systems, to methods for treating tamsulosin-responsive conditions such as benign prostatic hypertrophy (BPH), to pharmaceutical compositions formulated to administer tamsulosin transdermally, and to a low-temperature method for manufacturing a transdermal drug delivery system.

BACKGROUND

Benign prostatic hypertrophy (BPH) is a common disorder in men which becomes clinically manifest usually after age fifty. BPH is generally a progressive condition that in severe cases may compromise kidney function and require surgery. Untreated patients number over 37 million worldwide. In BPH, the hyperplastic prostate enlarges to compress or elongate the urethra and produces symptoms of urethral obstruction that may progress to urinary retention.

BPH is believed to be closely related to both aging and age-associated changes in circulating hormones such as androgens. In the normal prostate, the enzyme 5α-reductase in the epithelial cells converts testosterone, an androgen, to dihydrotestosterone (DHT). DHT, an active androgenic prostatic metabolite, binds cytoplasmic receptor and is transported to the nucleus, where it initiates RNA and protein synthesis and cell replication. BPH is believed to develop in response to the action of DHT on the aging prostate and to changes in stromal and epithelial cells. Steers & Zorn, *Dis. Mon.*, 41(7):437–497 (1995).

Clinical manifestations of BPH include both obstructive symptoms (e.g., hesitancy, weak stream, intermittency, and urinary retention) resulting directly from narrowing of the bladder neck and prostatic urethra by the hyperplastic prostate, as well as irritative lower urinary tract symptoms (e.g., urinary frequency, nocturia, dysuria, urgency, and urge incontinence). Left untreated, BPH may result in more severe complications of the urinary tract and kidneys, such as uraemia, urinary tract infection, acute urinary retention, and hydronephrosis. For an overview of BPH physiology and diagnosis, see, e.g., Blaivis, J., *Urology*, 32(6) (Suppl.):5–11 (1988); Walsh, P., in *Campbell's Urology*, 4th ed., 1248–1265, (Walsh et al., eds., W. B. Saunders Co. 1979); and Coffey, D., in *Campbell's Urology*, 4th ed., 233–274 (Walsh et al., eds., W. B. Saunders 1979).

BPH has been treated medically with some success using techniques such as partial prostatectomy, transurethral resection of the prostate (TURP), transurethral incision of the bladder neck, balloon dilatation of the prostate, treatment with sympathetic α-adrenergic inhibitors (to inhibit α-adrenoceptor-mediated contractions), antiandrogen therapy to atrophy the prostatic epithelium, urinary diversion by catheter, laser therapy, laser prostatectomies, hyperthermia, ultrasonic and radiofrequency ablation, transurethral microwave thermal therapy using a catheter (U.S. Pat. No. 5,464,437 to Reid et al.), and treatment with hydrolytic enzyme compositions (U.S. Pat. No. 5,116,615 to Gokcen & Guy). See, e.g., *Cecil Textbook of Medicine*, 19th ed., 1353 (Wyngaarden et al., eds., W. B. Saunders 1992).

Prostatitis, or inflammatory disease of the prostate, is believed to be due to bacterial infection of the prostate in approximately five percent of all cases, and is of unknown cause in the remaining cases. Prostatitis includes diseases such as chronic bacterial prostatitis, acute bacterial prostatitis, abacterial prostatitis, and prostatodynia; these diseases are distinguishable based on microscopic examination of expressed prostatic secretions (EPS) and quantitative bacterial localization cultures of urethral urine, bladder urine, and EPS.

Chronic bacterial prostatitis, or bacterial infection of the prostate, is believed to result from (1) urinary tract infection (bacteriuria) or (2) impairment of host defense mechanisms, as implicated by decreased concentrations of prostatic antibacterial factor, magnesium, zinc, calcium, citric acid, spermine, cholesterol, and lysozyme in prostatic fluid of men with chronic bacterial prostatitis. Chronic bacterial prostatitis is also believed to be a common cause of recurrent urinary tract infection in men. See, e.g., Fowler, J., Jr., in *Urinary Tract Infection and Inflammation*, 92–123 (Year Book Medical Publishers, 1989). Like chronic bacterial prostatitis, acute bacterial prostatitis is also associated with concomitant bacteriuria, and many of the symptoms, such as urinary frequency and dysuria, are similar; however, the onset of acute bacterial prostatitis is much faster and more severe than that of chronic bacterial prostatitis. Acute and chronic bacterial prostatitis have been treated by antibiotics therapy. See, e.g., Fair, ed., *Urology*, (1984). Chronic bacterial prostatitis has additionally been treated with suppressive antimicrobial therapies.

Little is known about abacterial prostatitis and prostatodynia, although their symptoms are similar to those of chronic bacterial prostatitis. In chronic abacterial prostatitis, EPS are abnormal but all bacterial cultures are negative. In prostatodynia, both EPS and cultures are negative. Abacterial prostatitis and prostatodynia have been treated with antimicrobial and antibiotic therapies and stress management, but the results of drug therapies have been disappointing.

Prostatic cancer is the second most common malignancy in American men. Prostatic cancer may produce symptoms of urethral obstruction which are indistinguishable from those produced by BPH, either by direct extension into the bladder or by spreading behind the bladder through the seminal vesicles. Like BPH, prostatic cancer increases in prevalence with patient age, requires androgens for growth and development, and responds to antiandrogen treatment regimens; most (approximately 80%) prostatic cancers arise with concomitant BPH. Bostwick, et al., *Cancer*, 70(1 Suppl): 291–301 (1992).

Prostatic cancer has been treated medically with some success through surgical techniques such as radical prostatectomy, and through radiation therapy via either external beam or surgical implants of interstitial radioactive seeds into the prostate. Hormonal therapies available include ablation by castration, administration of exogenous estrogens to deprive prostatic tumors of circulating androgens, releasing hormone analogues that inhibit testosterone synthesis, and/or administering antiandrogens which block androgen action in the prostate itself. Chemotherapy has yielded discouraging results. See, e.g., *Cecil Textbook of Medicine*, 19th ed., 1353 (Wyngaarden et al., eds., W. B. Saunders 1992).

Although a number of therapies have been proposed to treat each of these disorders, there remains a need in the art to provide a more effective and minimally invasive method of treating prostatic disorders such as BPH, prostatitis or prostatic cancer.

The present invention is directed to a novel treatment of these prostatic disorders. More specifically, the invention is directed to the transdermal administration of 5-[2-[[2-(2-ethoxyphenoxy)ethyl]amino]propyl]-2-methoxybenzenesulfonamide, or "tamsulosin," and relates primarily to a drug delivery system for administering tamsulosin transdermally.

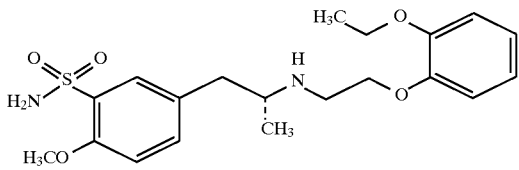

Tamsulosin

Tamsulosin is an $\alpha_1$-adrenergic receptor antagonist with efficacy in treating BPH and related disorders. The drug is described in U.S. Pat. No. 5,447,958 to Niigata et al., assigned to Yamanouchi Pharmaceutical Co., Ltd. Reference may be had thereto for any information concerning tamsulosin not explicitly included herein.

Currently, tamsulosin is administered orally or by injection. While, as alluded to above, the drug is quite effective in treating various prostatic disorders, drug non-compliance is a serious problem. Transdermal administration of tamsulosin, as disclosed and claimed herein, significantly enhances patient compliance by providing an advanced delivery system useful for administering the drug over an approximately three- to seven-day period.

There are a number of other advantages to administering tamsulosin transdermally as well: gastrointestinal and other side effects associated with oral administration are substantially avoided; continuous delivery provides for sustained blood levels; the transdermal patch is easily removable if any side effects do occur; and the likelihood of patient acceptance is significantly improved. The continuous delivery is especially advantageous for treatment of nocturia. In general, steady-state, transdermal delivery of the drug seems to provide a far better side effect profile overall than is associated with oral administration.

None of the art of which applicants are aware describes a specific transdermal drug delivery system which has been demonstrated to be effective in administering tamsulosin. Nor does the art set forth data on skin permeability or therapeutic administration rates with respect to such compounds. To the best of applicants' knowledge, then, the transdermal administration of tamsulosin is unknown and unsuggested by the art.

SUMMARY OF THE INVENTION

Accordingly, it is a primary object of the present invention to address the above-mentioned need in the art by providing a drug delivery system for the transdermal administration of tamsulosin.

It is another object of the invention to provide a drug delivery system for administering tamsulosin transdermally, which comprises a laminated composite of a backing layer and at least one polymeric adhesive layer which contains the drug.

It is still another object of the invention to provide a drug reservoir for use in a transdermal tamsulosin system.

It is yet another object of the invention to provide a method for administering tamsulosin to treat a tamsulosin-responsive condition, comprising transdermally delivering a pharmaceutically effective amount of the drug to an individual in need of such treatment.

It is a further object of the invention to provide for treating BPH by administering tamsulosin to a patient through a predetermined area of intact skin or mucosal tissue for a time period and at an administration rate effective to alleviate the symptoms of the condition.

It is still a further object of the invention to provide pharmaceutical compositions formulated for transdermal delivery of tamsulosin.

It is yet a further object of the invention to provide a low-temperature method for manufacturing a transdermal drug delivery system containing a volatile enhancer component.

Additional objects, advantages and novel features of the invention will be set forth in part in the description which follows, and in part will become apparent to those skilled in the art upon examination of the following, or may be learned by practice of the invention.

In one aspect of the invention, then, a drug delivery system for transdermal administration of tamsulosin is provided. The system is a laminated composite comprising a backing layer, a drug reservoir, and a means for affixing the composite to the skin. The drug reservoir and the affixing means may be distinct, such that a separate contact adhesive layer is provided which serves as the basal surface of the device, or the drug reservoir may itself be comprised of an adhesive layer which is suitable for contacting and adhering to the skin. Such therapeutic systems are in the nature of "solid matrix" type transdermal patches. In a preferred embodiment, the systems contain two drug reservoirs comprised of polymeric adhesive material, separated by an adsorbent source layer of a nonwoven fabric, wherein one of the reservoirs then serves as the basal surface of the device and adheres to the skin during use. The source layer enables the use of a low-temperature manufacturing process in which the drug formulation is deposited onto the source layer during device fabrication, using a "printing" technique, as will be explained in detail below.

In another aspect of the invention, a drug reservoir is provided which is comprised of a polymeric matrix material containing a tamsulosin formulation. Generally, the formulation will include a permeation enhancer composition selected to provide effective transdermal drug delivery when the reservoir is part of a transdermal tamsulosin system.

In another aspect of the invention, a method is provided for treating an individual with a tamsulosin-responsive condition or disease, such as BPH, prostatitis and prostatic cancer. The method involves administering a therapeutically effective amount of tamsulosin to the skin or mucosal tissue of the individual for a time period and at an administration rate effective to alleviate the symptoms of the condition or disease. The method is premised on the discovery that tamsulosin may be administered through the skin or mucosal tissue to achieve the desired systemic effects to which the present invention is addressed. In a preferred embodiment, a skin permeation enhancer composition is coadministered with the drug so as to increase permeability of the skin or mucosal tissue thereto and achieve more rapid delivery.

In still another aspect of the invention, tamsulosin-containing pharmaceutical compositions are provided which are formulated so as to be applied to the skin or mucosal tissue and effect delivery of the drug therethrough. The tamsulosin formulations contain a pharmaceutically acceptable transdermal vehicle and, preferably, a skin permeation enhancer composition to increase permeability of the skin or mucosal tissue to the drug.

In yet another aspect of the invention, a low temperature method is provided for manufacturing a transdermal tamsulosin drug delivery system containing a volatile enhancer component. The use of heat is avoided by printing the drug formulation onto an adsorbent adhesive-fabric laminate which is thereafter laminated to an adhesive-backing layer laminate.

BRIEF DESCRIPTION OF THE DRAWINGS

FIG. 1 illustrates in schematic form one embodiment of a transdermal delivery system which may be used in conjunction with the present invention.

FIG. 2 illustrates in schematic form one embodiment of a transdermal delivery system which may be used in conjunction with the present invention.

FIG. 3 is a graph illustrating the results from the vehicle screening studies described in Example 1.

FIG. 4 is a graph illustrating the results from the tamsulosin skin flux studies described in Example 2.

FIG. 5 is a graph illustrating the results from the tamsulosin skin flux studies described in Example 4.

FIG. 6 is a graph illustrating the results from the tamsulosin skin flux studies described in Example 5.

FIG. 7 is a graph illustrating the results from the tamsulosin skin flux studies described in Example 6.

FIG. 8 is a graph illustrating the results from the tamsulosin skin flux studies described in Example 7.

FIG. 9 is a graph illustrating the results from the tamsulosin skin flux studies described in Example 8.

FIG. 10 is a graph illustrating the results from the tamsulosin skin flux studies described in Example 9.

FIG. 11 is a graph illustrating the results from the tamsulosin skin flux studies described in Example 10.

DETAILED DESCRIPTION OF THE INVENTION

Before describing the present invention in detail, it is to be understood that this invention is not limited to particular formulations or transdermal systems as such may, of course, vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the content clearly dictates otherwise. Thus, for example, reference to "a permeation enhancer" includes a mixture of two or more permeation enhancers, reference to "a carrier" or "a vehicle" includes mixtures of carriers or vehicles, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

In describing and claiming the present invention, the following terminology will be used in accordance with the definitions set out below.

By "transdermal" delivery, applicants intend to include both transdermal (or "percutaneous") and transmucosal administration, i.e., delivery by passage of a drug through the skin or mucosal tissue and into the bloodstream.

By "therapeutically effective" amount is meant a nontoxic but sufficient amount of a compound to provide the desired therapeutic effect, in the present case, that dose of tamsulosin which will be effective in relieving symptoms of the condition or disease being treated. An "effective" amount of a permeation enhancer composition as used herein means an amount that will provide the desired increase in skin permeability and, correspondingly, the desired depth of penetration, rate of administration, and amount of drug delivered.

By "predetermined area of skin" is intended a defined area of intact unbroken living skin or mucosal tissue. That area will usually be in the range of about 5 $cm^2$ to about 100 $cm^2$, more usually in the range of about 10 $cm^2$ to about 100 $cm^2$, still more usually in the range of about 20 $cm^2$ to about 60 $cm^2$. However, it will be appreciated by those skilled in the art of transdermal drug delivery that the area of skin or mucosal tissue through which drug is administered may vary significantly, depending on patch configuration, dose, and the like.

"Penetration enhancement" or "permeation enhancement" as used herein relates to an increase in the permeability of skin to a pharmacologically active agent, i.e., so as to increase the rate at which the drug permeates through the skin and enters the bloodstream. The enhanced permeation effected through the use of such enhancers can be observed by measuring the rate of diffusion of drug through animal or human skin using a diffusion cell apparatus as described in the Examples herein.

"Carriers" or "vehicles" as used herein refer to carrier materials suitable for transdermal drug administration, and include any such materials known in the art, e.g., any liquid, gel, solvent, liquid diluent, solubilizer, or the like, which is nontoxic and which does not interact with other components of the composition in a deleterious manner. Examples of suitable carriers for use herein include water, silicone, liquid sugars, waxes, petroleum jelly, and a variety of other materials. The term "carrier" or "vehicle" as used herein may also refer to stabilizers, crystallization inhibitors, or other types of additives useful for facilitating transdermal drug delivery. It will be appreciated that compounds classified as "vehicles" or "carriers" may sometimes act as permeation enhancers, and vice versa, and, accordingly, these two classes of chemical compounds or compositions may sometimes overlap.

By the term "printed" as used herein is meant a substantially uniform deposition of the drug and/or enhancer formulation onto one surface of the source layer. As the source layer is comprised of a porous material, the drug and/or enhancer is initially retained by that layer, i.e., prior to equilibration, and then diffuses into one or both of the adjacent layers. It will be appreciated by those skilled in the art that a variety of techniques may be used to effect substantially uniform deposition of material, e.g., Gravure-type printing, extrusion coating, screen coating, spraying, painting, or the like.

One type of drug delivery system for transdermally administering tamsulosin is shown in FIG. 1. The system is in the form of a laminated composite, generally designated 10, comprising a backing layer 11, a reservoir layer 12 containing drug 12*a* either dispersed therein, or adsorbed or absorbed by a particulate hydrophilic material, and a release liner 13.

The backing layer 11 functions as the primary structural element of the device and provides the device with much of its flexibility, drape and, preferably, occlusivity. The material used for the backing layer should be inert and incapable of absorbing drug, enhancer or other components of the pharmaceutical composition contained within the device. The backing is preferably made of one or more sheets or films of a flexible material that serves as a protective covering to prevent loss of drug and/or vehicle via transmission through the upper surface of the device, and will preferably impart a degree of occlusivity to the device, such that the area of the skin covered on application becomes hydrated. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. Examples of materials useful for the backing layer are polyesters, polyethylene, polypropylene, polyurethanes and polyether amides. The layer is preferably in the range of about 15 microns to about 250 microns in thickness, and may, if desired, be pigmented, metallized, or provided with a matte finish suitable for writing.

The reservoir layer 12 in FIG. 1 doubles as the means for containing drug and as an adhesive for securing the device to the skin during use. That is, as release liner 13 is removed prior to application of the device to the skin, reservoir layer 12 serves as the basal surface of the device which adheres to the skin. Reservoir layer 12 is comprised of a pressure-sensitive adhesive suitable for long-term skin contact. It must also be physically and chemically compatible with tamsulosin and the carriers and vehicles employed. Suitable materials for this layer include, for example, polysiloxanes, polyisobutylenes, polyurethanes, plasticized ethylenevinyl acetate copolymers, low molecular weight polyether amide block polymers (e.g., PEBAX), tacky rubbers such as polyisobutene, polystyrene-isoprene copolymers, polystyrene-butadiene copolymers, and mixtures thereof. Presently preferred adhesive materials for use as reservoir layer 12 are polyisobutylenes, silicones and polyurethanes, with polyisobutylenes particularly preferred.

Preferably, the reservoir matrix in this embodiment additionally contains a dispersing agent which aids in maintaining the particulate phase dispersed in the continuous phase. In most cases, nonionic excipients such as lauric acid, propylene glycol monolaurate (PGML), myristyl lactate, lauryl lactate, or the like, facilitate dispersion.

In another embodiment, a polymer reservoir is provided containing sorbent particles as described in commonly assigned U.S. patent application Ser. No. 08/374,422, entitled "Polymer Adhesive Formulation Containing Sorbent Particles," published through the PCT as WO 96/22084. In this case, the polymer used is an adhesive that is substantially free of functional groups and by itself has acceptable cold flow properties (e.g., silicones, polyisobutylene, block co-polymers of polystyrene and polybutadiene/polyisoprene).

Excessive cold flow or poor adhesion may develop in transdermal matrix systems with high vehicle loadings. In the absence of other additives, the adhesive polymers may become plasticized by the vehicle. Furthermore, the vehicle, if loaded in excess of its solubility limits, may exude from the adhesive causing a decline in adhesion. For these reasons, porous sorbent materials are included in the adhesive. Sorbents typically constitute between 5% and 15% by weight of the components of the drug formulation, and are capable of absorbing about 10% to 50% by weight of these components. Examples of sorbent materials used for this purpose include porous silica gel, porous diatomaceous earth and sorptive nonwoven polymers. The polymer adhesives selected for use in the transdermal matrix system lack functional groups and, consequently, the drug and excipient preferentially adsorb to the sorbent particles, thereby providing greater flux.

The cold flow properties of the polymer adhesives of the present invention are considered acceptable when adhesion of the transdermal patch to the skin of the user remains high throughout the drug delivery period and the adhesive does not extend beyond the boundary of the patch.

Release liner 13 is a disposable element which serves only to protect the device prior to application. Typically, the release liner is formed from a material impermeable to the drug, vehicle and adhesive, and which is easily stripped from the contact adhesive. Release liners are typically treated with silicone or fluorocarbons. Silicone-coated polyester is presently preferred.

Figure 2:
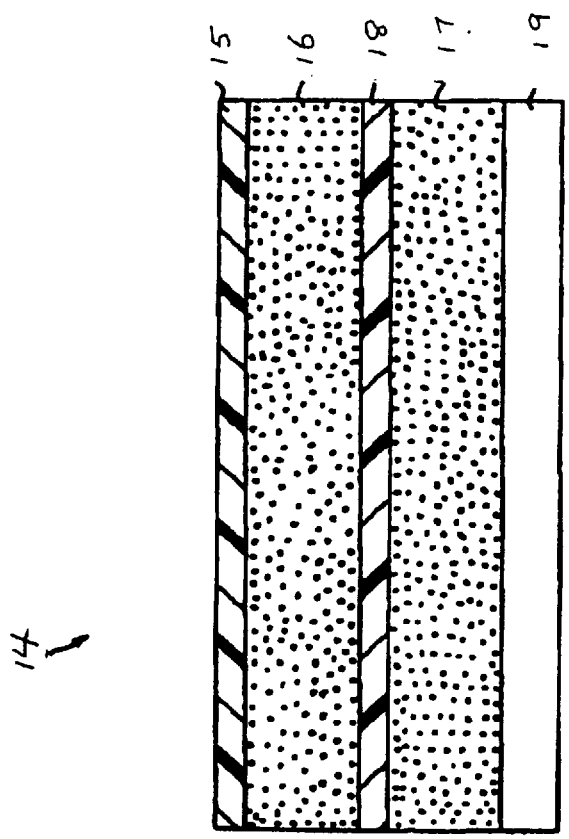

FIG. 2 illustrates a different type of laminated composite that may serve as the transdermal delivery system herein. That system is shown generally at 14, with backing layer 15, an upper, anchor adhesive layer 16, a lower contact adhesive 17, source layer 18 sandwiched between the two adhesive layers, and release liner 19. The backing layer and release liner are as described above with respect to the structure of FIG. 1. With regard to drug reservoir layers 16 and 17, suitable materials are as described above, e.g., polysiloxanes, polyisobutylenes, polyacrylates, polyurethanes, plasticized ethylene-vinyl acetate copolymers, low molecular weight polyether amide block polymers, tacky rubbers, and mixtures thereof.

The source layer 18 is a thin, flexible layer of an adsorbent material which provides the surface on which the drug formulation or components thereof are printed or otherwise deposited. The source layer allows a liquid formulation to be printed on its surface as a result of having surface properties not found in typical adhesive layers, and is positioned between the adhesive layers to eliminate adhesive cold flow. During fabrication, the drug and/or enhancer formulation is deposited in liquid form onto the source layer overlying the contact adhesive layer in a substantially uniform pattern. The source layer should be of a material capable of transiently adsorbing the formulation deposited thereon such that the formulation will not be displaced from the layer during the lamination process and its diffusibility into the adhesive layer in the assembled transdermal patch will not be impaired. For the foregoing reasons, a non-woven material such as polyethylene, polypropylene, polyamides, cotton, rayon or 100% non-woven polyester approximately 0.0011" to 0.010" thick is preferred.

The adhesive reservoir layers in these systems will generally although not necessarily range in thickness from about 1 to about 25 mils, preferably in the range of approximately 1 to 15 mils. If two or more reservoir layers are used, the reservoir layers in combination should meet the aforementioned thickness criteria. However, the thickness of the reservoir will depend, however, on a variety of considerations, including the quantity of drug to be incorporated in the reservoir, desired patch size, and the like.

It will be appreciated by those skilled in the art that variations on the aforementioned systems can be provided wherein still additional drug reservoir layers are included, along with source layers, such as of nonwoven fabric, therebetween.

The tamsulosin-containing pharmaceutical formulations present in the drug reservoirs of the above-described transdermal systems will preferably contain a permeation enhancer composition.

Suitable enhancers include, but are not limited to, dimethylsulfoxide (DMSO), N,N-dimethylacetamide (DMA), decylmethylsulfoxide ($C_{10}MSO$), polyethylene glycol monolaurate (PEGML), propylene glycol (PG), PGML, glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. The permeation enhancer may also be a vegetable oil as described in commonly assigned U.S. Pat. No. 5,229,130 to Sharma. Such oils include, for example, safflower oil, cotton seed oil and corn oil.

Additional enhancers for use in conjunction with the present invention are lipophilic compounds having the formula $[RCOO]_nR'$, wherein n is 1 or 2 and R is $C_1$–$C_{16}$ alkyl optionally substituted with 1 or 2 hydroxyl groups, and R' is hydrogen or $C_1$–$C_{16}$ alkyl optionally substituted with 1 or 2 hydroxyl groups. Within this group, a first subset of compounds are represented by the formula $[CH_3(CH_2)_mCOO]_nR'$ in which m is an integer in the range of 8 to 16, n is 1 or 2, and R' is a lower alkyl ($C_1$–$C_3$) residue that is either unsubstituted or substituted with one or two hydroxyl groups. Preferred enhancers within this group include an ester which is a lower alkyl ($C_1$–$C_3$) laurate (i.e., m is 10 and n is 1) such as "PGML." It will be appreciated by those skilled in the art that the commercially available material sold as "PGML" is typically although not necessarily a mixture of propylene glycol monolaurate itself, propylene glycol dilaurate, and either propylene glycol, methyl laurate, or both. Thus, the terms "PGML" or "propylene glycol monolaurate" as used herein are intended to encompass both the pure compound as well as the mixture that is typically obtained commercially. Also within this group is a second subset of compounds, namely, esters of fatty alcohols represented by the formula $CH_3(CH_2)_m$—O—CO—$CHR^1R^2$, in which $R^1$ and $R^2$ are independently hydrogen, hydroxyl, or lower alkyl ($C_1$–$C_3$), and m is as above. Particularly preferred enhancers within this group are lauryl lactate and myristyl lactate. In addition, a third subset of compounds within this group are analogous fatty acids, i.e., acids having the structural formula $CH_3(CH_2)_mCOOH$ where m is as above. A particularly preferred acid is lauric acid.

Other enhancer compositions are wherein a lipophilic compound as just described, particularly PGML, is combined with a hydrophilic compound, such as a $C_2$–$C_6$ alkanediol. One preferred hydrophilic enhancer within this group is 1,3-butanediol. Such enhancer compositions are described in detail in PCT Publication No. WO 95/05137, published Feb. 23, 1995. Another hydrophilic enhancer that may be included in these compositions is an ether selected from the group consisting of diethylene glycol monoethyl ether (Transcutol®) and diethylene glycol monomethyl ether. Such enhancer compositions are described in detail in U.S. Pat. Nos. 5,053,227 and 5,059,426 to Chiang et al., both of common assignment herewith. Butyrolactone may also formulated into the enhancer composition.

A particularly preferred enhancer composition for use in conjunction with the transdermal administration of tamsulosin, as provided herein, is a three-component composition containing: a lipophilic compound having the formula $[RCOO]_nR'$, wherein n, R and R' are as above, preferably a lipophilic compound having the formula $[CH_3(CH_2)_mCOO]_nR$ or $CH_3(CH_2)_m$—O—CO—$CHR^1R^2$ in which m, n, R, $R^1$, and $R^2$ are as defined above; and a hydrophilic compound selected from the group consisting of diethylene glycol monoethyl ether, diethylene glycol monomethyl ether, PG, 1,3-butanediol, and butyrolactone optionally substituted with one or two hydroxyl, lower alkyl ($C_1$–$C_3$), lower alkoxy ($C_1$–$C_3$), halogen and amino groups. The relative amounts of the three components in this enhancer composition are preferably, although not necessarily, as follows: (1) about 1 wt. % to 20 wt. %, preferably 1 wt. % to 10 wt. %, more preferably 5 wt. % of the lipophilic compound; (2) about 1 wt. % to 20 wt. %, preferably about 6 wt. % to 10 wt. %, more preferably 7 wt. % of the fatty acid compound; and (3) about 60 wt. % to 95 wt. %, preferably 70 wt. % to 90 wt. %, more preferably 85 wt. % of the hydrophilic compound.

The enhancer composition may also contain a solubilizer. Examples of suitable solubilizers include tertiary carboxylic acids, dimer acids, EMPOL®, and the like. When present, the solubilizer will constitute about 1 wt. % to about 5 wt. %, preferably about 2.0 wt. %, of the enhancer composition.

The amount of enhancer composition present in the drug formulation will depend on a number of factors, e.g., the strength of the particular enhancer composition, the desired increase in skin permeability, and the amount of drug which is necessary to deliver.

Other components that may be included in the drug formulation include carriers, tackifiers, pigments, dyes, and other additives that do not adversely affect the mechanical or adhesive properties of the formulation.

The present transdermal drug delivery systems can be fabricated using conventional coating and laminating techniques and equipment which are known to those skilled in the art, and/or explained in the literature. In general, devices of the invention are fabricated by solvent evaporation film casting, melt extrusion, thin film lamination, die cutting, or the like.

When a heat-sensitive and/or volatile component is incorporated into the composition, e.g., a component in an enhancer formulation, a manufacturing technique which avoids heat should be used. A "printing" technique as described in U.S. Pat. No. 4,915,950 is suitable for use in manufacturing the device of the present invention when a volatile component such as may be present in the skin permeation enhancer herein is included in the drug formulation. This technique will generally involve laminating the source layer to an adhesive layer, printing the drug/enhancer formulation onto the exposed surface of the source layer, and laminating the source layer to the second adhesive layer. This deposition method does not require the use of heat.

The present method of transdermally delivering tamsulosin may vary, but necessarily involves application of a composition containing tamsulosin to a predetermined area of the skin or mucosal tissue for a period of time sufficient to provide an effective blood level of drug for a desired period of time. The target flux of tamsulosin is at minimum approximately 0.50 $\mu g/cm^2/hr$ for a 30 $cm^2$ system to provide a physiologically effective dose, e.g., a blood level of approximately 5–10 ng/ml, preferably about 7 ng/ml.

The method may involve direct application of the composition as an ointment, gel, cream, or the like, or may involve use of a drug delivery device as taught in the art, as explained above. Ointments, gels, creams, or the like must be suitable for transdermal administration of a drug, i.e., must contain pharmaceutically acceptable excipients compatible with application to the skin or mucosal tissue, and will contain a sufficient amount of an enhancer composition as explained above. Preferably, transdermal formulations which are not in a "patch" structure but rather in an ointment, gel or the like, will contain the three-component enhancer composition described above, and will typically contain on the order of about 0.01 wt. % to 10 wt. % drug, and about 1.0 wt. % to 25.0 wt. % enhancer composition, with the remainder of the composition comprising a carrier or vehicle.

The transdermal tamsulosin delivery system of the present invention is designed for use in the treatment of benign prostatic hypertrophy and other disorders of the prostate gland that contribute to increased intraurethral pressure and urinary tract obstruction. The delivery of the alpha 1-adrenoceptor antagonist tamsulosin to adrenoceptors of the prostate is expected to inhibit the prostatic smooth muscle contractions responsible for the increased intraurethral pressure and thereby alleviate the urinary tract obstruction. The tamsulosin delivery system described herein provides a non-invasive method for the controlled delivery of a highly polar compound to the prostatic receptors at a sufficient rate for therapeutic benefit. The advantages of such a system include increased patient compliance and the ability to control the dosage of the drug.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric.

All patents, patent applications, and publications mentioned herein, both supra and infra, are hereby incorporated by reference.

Experimental

Materials:

Tamsulosin free base was provided by Yamanouchi Pharmaceutical Co., Tokyo, Japan. The polyisobutylene (PIB) adhesive was formulated with GRAS components. All other chemicals were medical or reagent grade.

Preparation of Prototype Systems:

The prototype system, composed of two adhesive layers with a nonwoven mat sandwiched therebetween, was prepared as follows.

Pre-blended PIE (the PIE blend contains a high molecular weight PIE (Exxon Vistanex® MML-100, M.W. 1,060,000–1,440,000), a low molecular weight PIE (Exxon Vistanex® LM-MS-LC, M.W. 42,600–46,100), and polybutene (Amoco Indopol® H-1900, M.W. 2300)), sorbent materials, and solubilizers were compounded in a sigma blade mixer to form a masterbatch. The masterbatch, tamsulosin, and fatty acid component of the enhancer composition were fed into a twin screw extruder. The drug and fatty acid enhancer were added via powder addition equipment. The coating weight of the extrudate was adjusted to 17.5 mg/cm$^2$ by passing the extrudate, sandwiched between release liners, through a nip. One liner was stripped and replaced by either a nonwoven mat or a backing film. Two laminates resulted: (1) the nonwoven mat/adhesive/liner laminate (the "nonwoven laminate"); and (2) the backing film/adhesive/liner laminate (the "backing laminate").

The nonwoven laminate was then printed with the lipophilic and hydrophilic components of the enhancer composition. The liner was stripped from the backing laminate and the remaining backing-adhesive layers were then laminated to the printed nonwoven laminate. The result was a five-layer construction as illustrated in FIG. 2.

In Vitro Skin Permeation of Tamsulosin:

Skin Preparation: Human cadaver skin was used for the permeation studies. Frozen skins were thawed and the epidermal layers (stratum corneum and viable epidermis) were separated from the full-thickness skin by immersion thereof in water at 60° C. for two min. This epidermis was either used immediately for flux studies or stored at −20° C. for later studies.

Skin Permeation from Vehicles: Modified Franz diffusion cells were used for evaluating the performance of vehicles for tamsulosin delivery. The receiver compartment was filled with 7.5 ml of pH 7.0 phosphate buffer. Two hundred $\mu$l of the selected vehicles saturated with tamsulosin were then placed in the donor chamber to initiate the skin flux experiments. The temperature of the diffusion cell contents was maintained at 32°±1° C. At predetermined times, one ml of receiver content was withdrawn and replaced with fresh buffer. Samples were assayed by HPLC as described below.

Skin Permeation from Prototypes: Modified Franz cells were used for evaluating the prototype systems for delivery of tamsulosin. The prototype systems were peeled off the release liner and placed on top of the epidermis with the drug adhesive layer facing the stratum corneum. Gentle pressure was applied to insure full contact between the drug adhesive layer and the stratum corneum. The skin membrane with the tamsulosin prototype system was then mounted carefully between the donor and the receiver compartments. The receiver compartment was filled with pH 7 buffer and the temperature was maintained at 32°±1° C. throughout the experimental period. Seven and one-half ml of receiver content was withdrawn and replaced with fresh buffer. Samples were assayed by HPLC as described below.

Flux Determination: Skin flux ($\mu$g/cm$^2$/hr) was determined from the steady-state slope of the plot of the cumulative amount of tamsulosin permeated through the skin versus time. Three to six replicates of each formulation were assayed.

HPLC Method:

A reverse-phase HPLC (Shimadzu) with a 4.6×125 mm Nucleosil 100 C18 column was used. The mobile phase was 27% acetonitrile and 73% 0.005N perchloric acid aqueous solution. The flow rate was at 0.9 mL/min with detection at 280 nm. The retention time of tamsulosin was approximately 5 minutes. The area under the peak was used to calculate the concentration and the range of the calibration curve was from 0.5 mg/mL to 20 mg/mL.

EXAMPLE 1

Vehicle Screening Studies

The purpose of the initial vehicle screening studies was to examine the effect of combinations of skin permeation enhancers on tamsulosin skin flux. Three different classes of skin permeation enhancers have been combined in this study. Class A enhancers are fatty acids (lauric acid, oleic acid, palmitic acid, myristic acid, stearic acid, and the like), class B enhancers are hydrophilic compounds which solubilize the tamsulosin drug substance (for example, Transcutol®, 1,3-butanediol, butyrolactone), and the class C vehicles are lipophilic esters (e.g., methyl laurate, lauryl lactate, myristyl lactate, PGML, and the like). The experiments were conducted with saturated tamsulosin solutions so that differences in the flux related to skin permeability and not to the thermodynamic activity of the drug substance in the liquid vehicle. The results from flux studies are depicted in FIG. 3.

Figure 3:
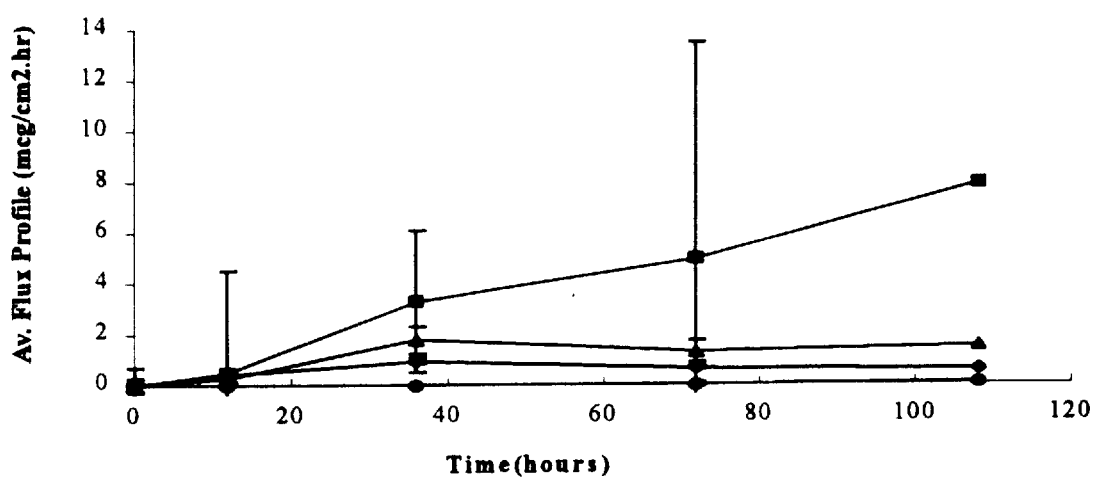

FIG. 3 shows that high tamsulosin flux was achieved with the three-component vehicle system lauric acid (A1), 1,3-butanediol (B2), and methyl laurate (C1). Tamsulosin average flux profile ($\mu$g/cm$^2$/hr) as a function of time was determined for the following combinations of enhancer components in weight percent (lauric acid:1,3-butanediol:methyl laurate): 5%:80%:15% (squares); 5%:50%:45% (triangles); 5%:20%:75% (diamonds); and, 5%:95%:0% (ovals).

The formulation containing none of the lipophilic vehicle, methyl laurate, has a lower skin flux. Furthermore, the ratio of 1,3-butanediol:methyl laurate impacts the flux. For example, the highest flux is observed in the formulation which contains an 8:1.5 ratio of 1,3-butanediol:methyl laurate. These results demonstrate that high tamsulosin skin flux was achieved in the presence of all three vehicle classes.

EXAMPLE 2

Skin Flux Results: Effect of Hydrophilic and Lipophilic Enhancers

Figure 4:
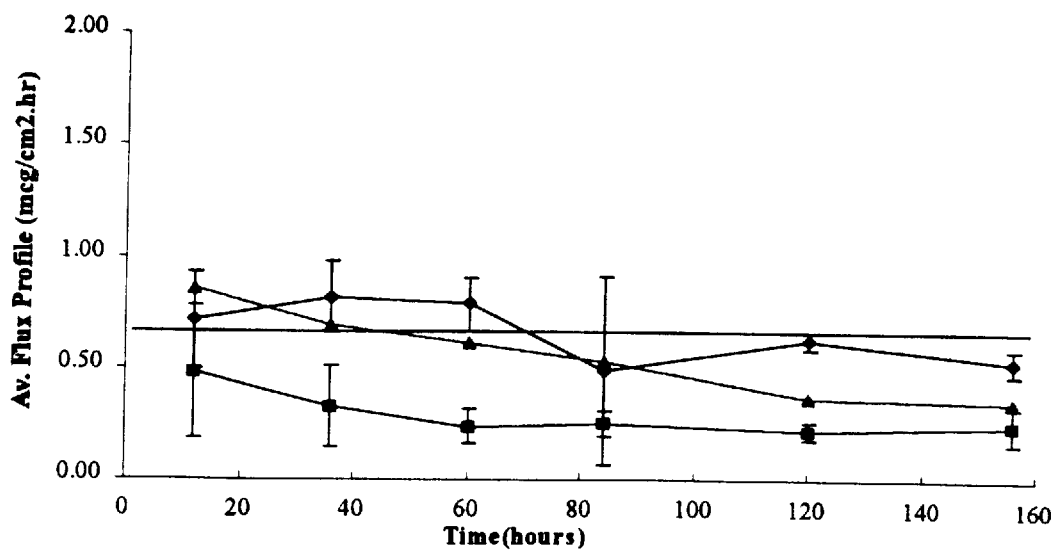

The base formulation in this experiment consisted of a PIB adhesive which contained 5% tamsulosin, 5% lauric acid, and 15% silica gel 74 in a PIB adhesive. The Transcutol®:PGML vehicle combination (8:2) was added later so that it comprised 20% or 25% by weight of the formulation. FIG. 4 demonstrates that there was little difference between the 20% (triangles) and 25% (diamonds) enhancer additions. Furthermore, FIG. 4 indicates that the use of 25% Transcutol®, with none of the lipophilic enhancer (squares), gives a significantly lower skin flux.

EXAMPLE 3

Skin Flux Results: Effect of Drug and Fatty Acid Loading

The flux studies described in Examples 1 and 2 were done using prototypes in which drug loading was in excess of its solubility so that the adhesive matrices were at saturation. The studies described in this example were done to investigate tamsulosin flux using decreased drug and lauric acid (A1) loadings, as well as to investigate the effect on tamsulosin flux of two ratios of the Transcutol®:PGML vehicle combination (1:1 and 8:2). Two different skins were included in this study, skin 95-05 and skin 95-25. It was evident that the 95-25 skin is lower in permeability because comparable formulations gave lower skin flux with the 95-25 skin than with the 95-05 skin.

In a separate experiment, two starting adhesive compositions were used in this study: 1) 3% tamsulosin, 3% lauric acid, and 15% silica gel 244 in a PIB adhesive; and 2) 2% tamsulosin, 2% lauric acid, and 15% silica gel 244 in a PIB adhesive. The enhancer combination Transcutol®:1,3-butanediol (1:1) was added later at two different loadings, 20% and 25% by weight of the formulation. The Transcutol®:1,3-butanediol vehicle combination (8:2) was added at only 20% by weight of the formulation. The low permeability skin, 95-25, showed little difference between the 1:1 and 8:2 Transcutolφ:1,3-butanediol combinations. Results obtained using the higher permeability skin indicated that the 1:1 Transcutol®:1,3-butanediol combination resulted in lower flux than the 8:2 combination in the 2% tamsulosin, 2% lauric acid formulation. Both the 1:1 and 8:2 formulations gave identical skin flux results for the 3% tamsulosin, 3% lauric acid formulation using the higher permeability skin. Results obtained using either skin type suggested that an optimal formulation for drug and lauric acid loadings are 3% rather than 2%.

EXAMPLE 4

Skin Flux Results: Effect of Drug:Fatty Acid Ratio

Figure 5:
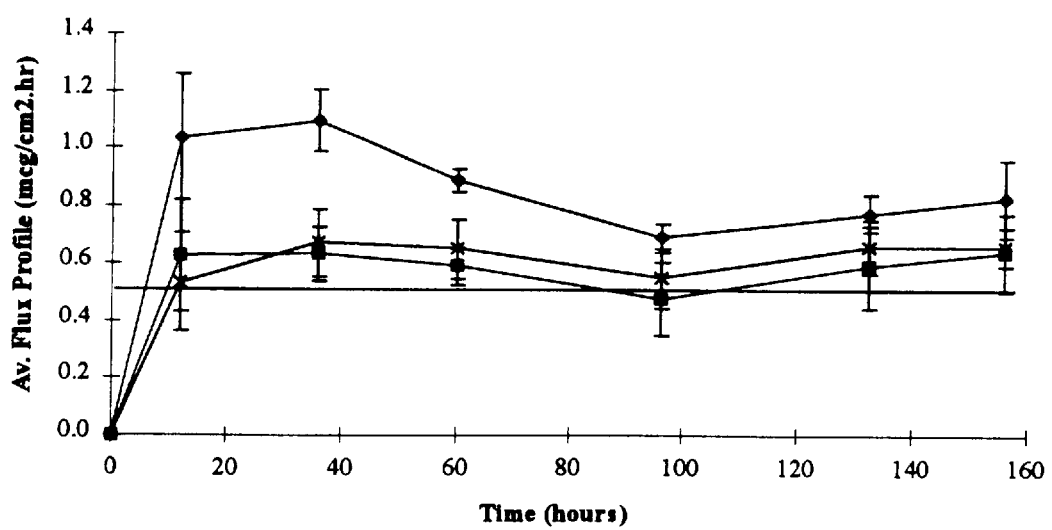

This following flux study was performed to examine how variations in the ratio of tamsulosin:lauric acid affected tamsulosin skin flux. The base formulation contained 5% lauric acid and 15% silica gel 244 in a PIB adhesive. The results of these studies, in which the ratio of tamsulosin to lauric acid was varied at 2:5 (squares), 3:5 (X), and 4:5 (diamonds), shown in FIG. 5, suggest that higher fluxes might be achieved with tamsulosin:lauric acid ratios closer to 1:1.

EXAMPLE 5

Skin Flux Results: Effect of Various Fatty Acids

Figure 6:
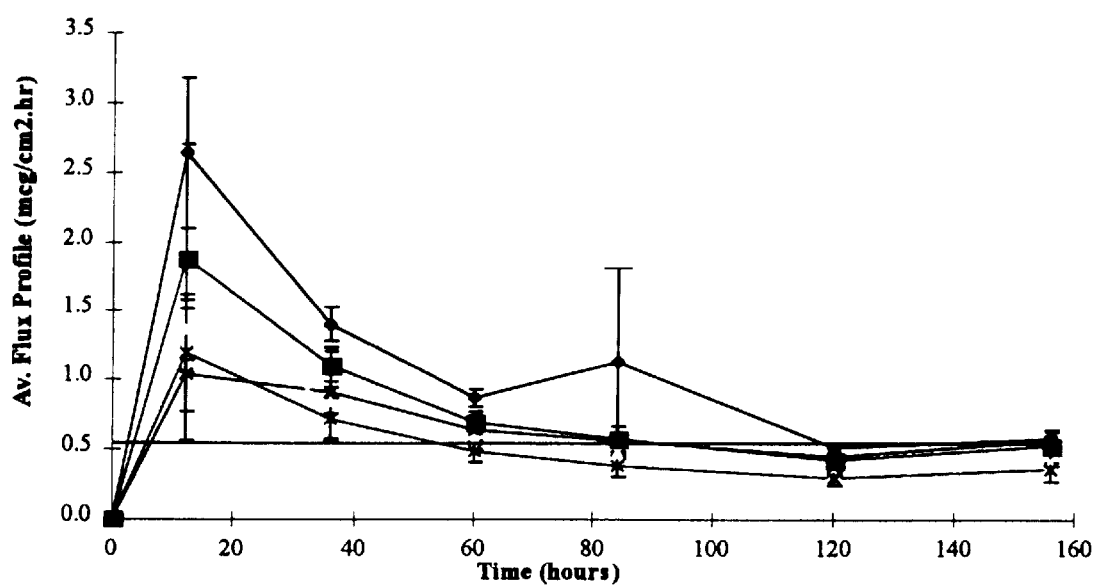

The following flux study was done to investigate the effect of different fatty acids on tamsulosin skin flux. An adhesive formulation was prepared which contained 5% tamsulosin, 5% lauric acid (A1; diamonds), oleic acid (A2; X), palmitic acid (A3; triangles), myristic acid (A4; squares), or stearic acid (A5, *), and 15% silica gel 244. The vehicle combination Transcutol®:1,3-butanediol (8:2) was added later so that it comprised 25% of the formulation. The results depicted in FIG. 6 indicate that variation of the fatty acid has an effect at the earlier flux timepoints with lauric acid giving the highest initial fluxes. The tamsulosin flux profiles observed with the different fatty acids converged to a similar value at later timepoints. This observation indicates that the achievement of a steady state plasma concentration of tamsulosin from a transdermal system can be modified by varying the fatty acid component of the adhesive formulation. In addition, these results indicate that tamsulosin delivery can be varied as desired over both the first three days as well as the entire the seven day duration of tamsulosin delivery.

EXAMPLE 6

Skin Flux Results: Effect of Tamsulosin Loading

Figure 7:
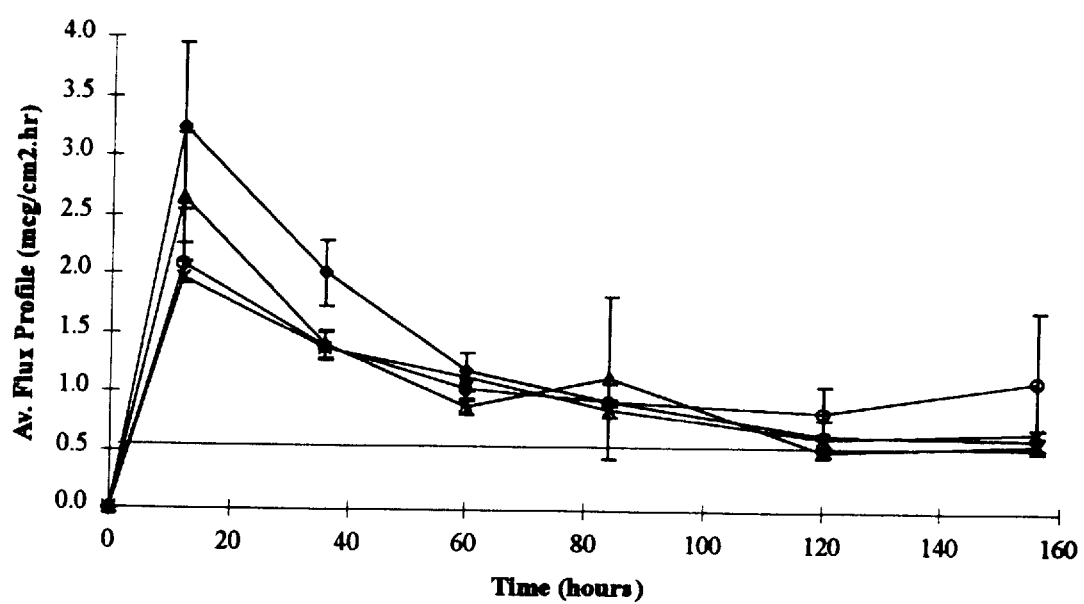

This flux experiment was performed to determine if tamsulosin loadings could be reduced without compromising skin flux. The results depicted in FIG. 7 show that different loadings of tamsulosin (2%, circles; 3%, X; 4%, diamonds; and 5%, triangles) and lauric acid at a 1:1 ratio do not change the flux.

EXAMPLE 7

Skin Flux Results: Comparison of the Effect of Transcutol® and Butyrolactone Enhancer Compounds The preceding flux studies demonstrate that the target flux can be achieved using a range of skin permeation enhancer ratios and fatty acids. The following studies were done to examine whether the hydrophilic component of the enhancer formulation can be varied as well.

Figure 8:
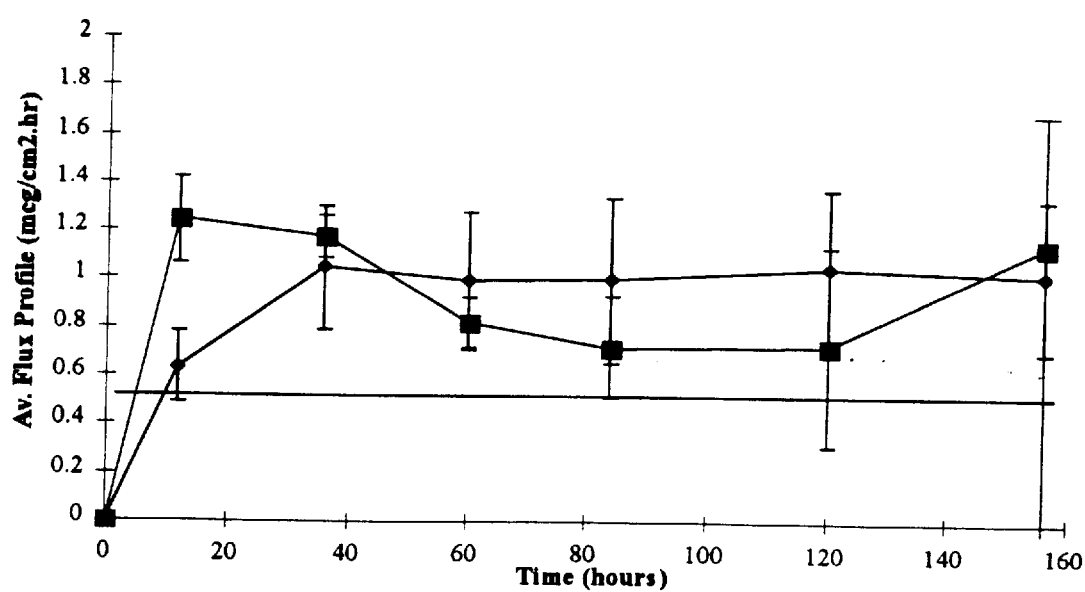

The results shown in FIG. 8 indicate that hydrophilic vehicle butyrolactone (diamonds) can be substituted for vehicle Transcutol® (squares) without adversely impacting the flux. The formulations were composed of 5% tamsulosin, 5% lauric acid, and 15% silica gel 244 in a PIB adhesive. A 25% Transcutol®:PGML (8:2) formulation gave comparable skin flux to the new butyrolactone: PGML formulation.

EXAMPLE 8

Skin Flux Results: Effect of 1,3-Butanediol Hydrophilic Enhancer Compound

Figure 9:
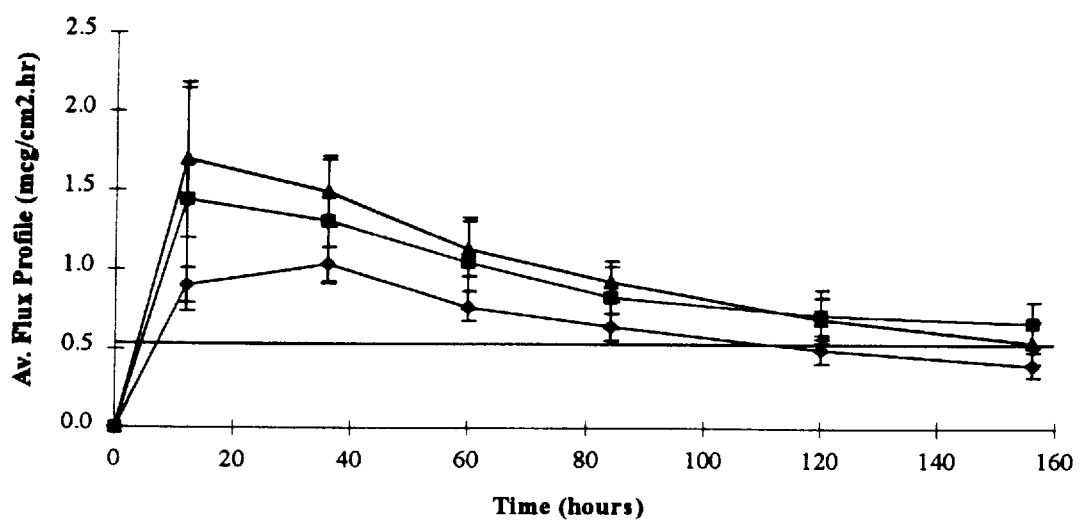

The results shown in FIG. 9 indicate that a third hydrophilic vehicle, 1,3-butanediol, also can provide the target tamsulosin skin flux. The base formulation used in this study contained 5% tamsulosin, 5% lauric acid, and 15% silica gel 244 in a PIB adhesive. The vehicle combination, 1,3-butanediol:PGML, was varied at 8:2 (squares), 1:1 (triangles), and 2:8 (diamonds), and constituted 25% of the formulation. The results demonstrate that all ratios of 1,3-butanediol:PGML deliver the target flux. The formulations containing 1:1 or 8:2 ratios of 1,3-butanediol:PGML appear to provide a greater initial flux and more prolonged steady state flux levels.

EXAMPLE 9

Skin Flux Studies: Effect of Adhesive Composition

Figure 10:
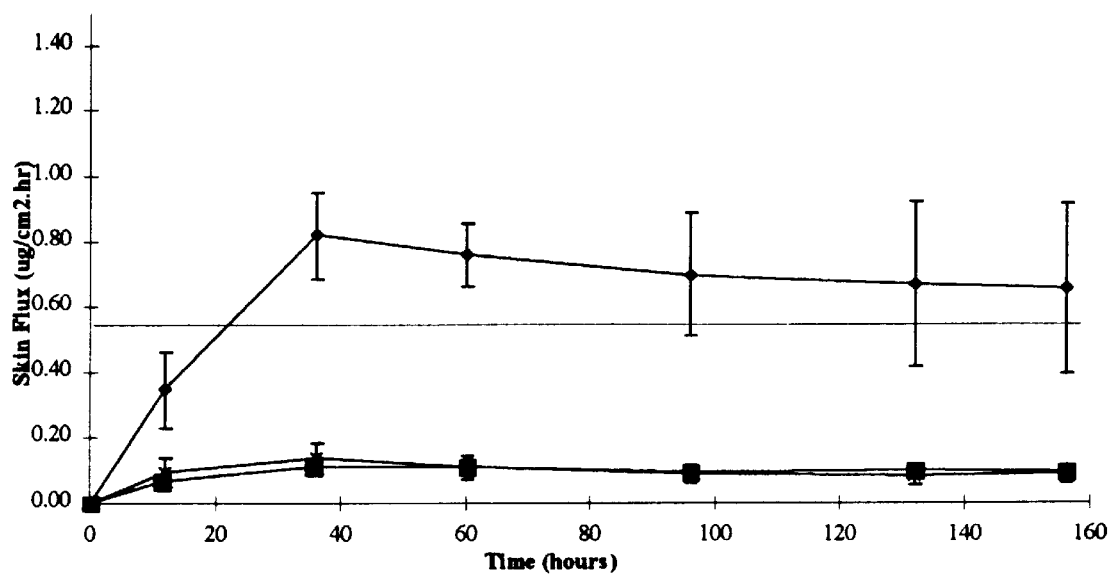

The studies described in this example were conducted to compare tamsulosin skin flux from prototypes fabricated using a PIB adhesive as described herein with flux from prototypes made from Durotak® 2287 (National Starch, Bridgewater, N.Y.), a noncrosslinking acrylate-based pressure sensitive adhesive, as described in U.S. Pat. No. 5,503,843 to Santus et al. Three starting adhesive compositions were used in this study: (1) 10% tamsulosin, 10% oleyl alcohol, 10% N-methyl-2-pyrrolidone and 70% Durotak® 2287 adhesive (squares); (2) 10% tamsulosin, 0.9% PGML, 1.5% lauric acid, 17.6% 1,3-butanediol and 70% Durotak® 2287 adhesive (diamonds); and (3) [2% tamsulosin, 2% lauric acid, 0.5% EMPOL® 1008 (Henkel Corp., Ambler, Pa.), 15% silica gel 244 and 80.5% PIE (2:4:4 Exxon Vistanex® MML-100:Exxon Vistanex® LM-MS-LC:Amoco Indopol® H-19001 and 25% [9.5:0.5 1,3-butanediol:PGML] (X). The results obtained in these studies (see Table 1 and FIG. 10) indicate that the target flux was achieved only with the PIB-based adhesive composition and not with either of the two acrylate-based adhesive systems.

TABLE 1

Comparative Tamsulosin Flux Data

| Formulation (Figure symbol) | Average Flux ($\mu g/cm^2/hr$) | Standard Deviation |
| --- | --- | --- |
| (1) | 0.099 | 0.003 |
| (2) | 0.100 | 0.010 |
| (3) | 0.658 | 0.071 |

EXAMPLE 10

Low-Temperature Manufacture of the Prototype System

One possible restriction on the preparation of the tamsulosin transdermal delivery system may be imposed by the high adhesive coating weight. A high coating weight, approximately 35 mg/cm², is preferred because the vehicles may be depleted from delivery systems having lower coating weights. This depletion may result in a substantially decreased skin flux during the later stages of wear. The high coating weight is difficult to achieve economically using traditional solvent coating methods because multiple coating passes at slow line speeds would be used to remove all solvent. Therefore, an evaluation of tamsulosin skin flux was conducted under conditions comparable to those for preparing a high-coating weight prototype by melt extrusion.

Figure 11:
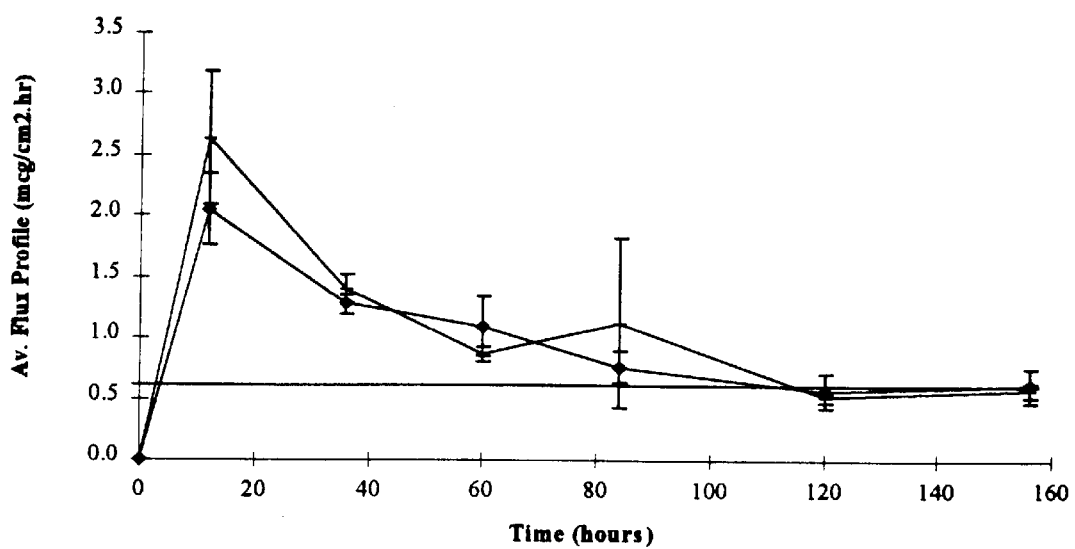

Various solvent-coated systems were subjected to high-temperature conditions to mimic the extrusion process. Both the heat-treated and solvent cast systems were compared in a skin flux study. The results shown in FIG. 11 indicate that the heat-treated sample skin flux (diamonds) is comparable to the skin flux from solvent coated system (+).

We claim:

1. A drug delivery system for the transdermal administration of tamsulosin, comprising a laminated composite of:
   a backing layer that is substantially impermeable to tamsulosin; and
   at least one polymeric reservoir layer containing a drug formulation comprised of tamsulosin and a skin permeation enhancer composition effective to facilitate permeation of a therapeutically effective amount of tamsulosin through the skin or mucosal tissue,
   wherein the skin permeation enhancer composition comprises: (i) a lipophilic compound having the formula [RCOO]$_n$R', wherein n is 1 or 2, and R and R' may be the same or different and are $C_1$–$C_{16}$ alkyl optionally substituted with 1 or 2 hydroxyl groups, (ii) an acid having the formula $CH_3(CH_2)_m COOH$ where m is an integer in the range of 8 to 16: and (iii) a hydrophilic compound selected from the group consisting of diethylene glycol monoethyl ether, diethylene glycol monomethyl ether, propylene glycol, 1,3-butanediol, and butyrolactone optionally substituted with one or two hydroxyl, lower alkyl ($C_1$–$C_3$) lower alkoxy ($C_1$–$C_3$), halogen and amino groups.

2. The system of claim 1 wherein the size of the system and the type and amount of the permeation enhancer composition are selected to provide a transdermal flux of tamsulosin at least about 0.5 $\mu g/cm^2/hr$ over a predetermined time period.

3. The system of claim 2, wherein the predetermined time period is approximately seven days.

4. The system of claim 1, comprising two polymeric reservoir layers separated by a source layer.

5. The system of claim 1, wherein the lipophilic compound is an ester selected from the group consisting of a compound having the formula $(CH_3(CH_2)_m COO]_n R'$ and a compound having the formula $CH_3(CH_2)_m$—O—CO—$CHR^1R^2$, in which m is an integer in the range of 8 to 16, n is 1 or 2, R' is a lower alkyl ($C_1$–$C_3$) residue that is either unsubstituted or substituted with one or two hydroxyl groups, and $R^1$ and $R^2$ are independently hydrogen, hydroxyl or lower alkyl.

6. The system of claim 1, wherein the permeation enhancer composition comprises propylene glycol monolaurate, lauric acid, and 1,3-butanediol.

7. The system of claim 1, wherein the reservoir layer is comprised of a pharmaceutically acceptable pressure-sensitive contact adhesive.

8. The system of claim 7, wherein the contact adhesive comprises a continuous hydrophobic polymer phase containing a particulate phase of an inorganic silicate dispersed therein.

9. The system of claim 8, wherein the continuous polymer phase further comprises a dispersing agent for maintaining the dispersion of the particulate phase therein.

10. The system of claim 9, wherein the dispersing agent is a nonionic solubilizing compound.

11. The system of claim 10, wherein the nonionic solubilizing agent is selected from the group consisting of lauric acid, propylene glycol monolaurate (PGML), myristyl lactate, and lauryl lactate.

12. The system of claim 7, wherein the contact adhesive comprises:
    a polymer that is substantially free of functional groups and which, by itself, has cold flow properties selected to provide for effective adhesion of the system to the skin; and
    a porous sorbent material that-sorbs a sufficient amount of the drug formulation to maintain the cold flow properties of the adhesive at an acceptable level.

13. The system of claim 7, wherein the adhesive is polyisobutylene.

14. A drug reservoir comprising:
    at least one polymeric reservoir layer; and
    a drug formulation comprised of tamsulosin and a skin permeation enhancer composition effective to facilitate permeation of a therapeutically effective amount of tamsulosin through the skin or mucosal tissue wherein the skin permeation enhancer composition comprises: (i) a lipophilic compound having the formula $[RCOO]_nR'$, wherein n is 1 or 2, and R and R' may be the same or different and are $C_1$–$C_{16}$ alkyl optionally substituted with 1 or 2 hydroxyl groups, (ii) an acid having the formula $CH_3(CH_2)_mCOOH$ where m is an integer in the range of 8 to 16; and (iii) a hydrophilic compound selected from the group consisting of diethylene glycol monoethyl ether, diethylene glycol monomethyl ether, propylene glycol, 1,3-butanediol, and butyrolactone optionally substituted with one or two hydroxyl, lower alkyl ($C_1$–$C_3$), lower alkoxy ($C_1$–$C_3$) halogen and amino groups.

15. The drug reservoir of claim 14 wherein the size of the reservoir and the type and amount of the permeation enhancer composition are selected to provide a transdermal flux of tamsulosin at least about 0.5 $\mu g/cm^2/hr$ over a predetermined time period.

16. The drug reservoir of claim 15, wherein the predetermined time period is approximately seven days.

17. The drug reservoir of claim 14, wherein the lipophilic compound is an ester selected from the group consisting of a compound having the formula $[CH_3(CH_2)_mCOO]_nR'$ and a compound having the formula $CH_3(CH_2)_m$—O—CO—$CHR^1R^2$, in which m is an integer in the range of 8 to 16, n is 1 or 2, R' is a lower alkyl ($C_1$–$C_3$) residue that is either unsubstituted or substituted with one or two hydroxyl groups, and $R^1$ and $R^2$ are independently hydrogen, hydroxyl or lower alkyl.

18. The drug reservoir of claim 14, wherein the permeation enhancer composition comprises propylene glycol monolaurate, lauric acid, and 1,3-butanediol.

19. The drug reservoir of claim 14, wherein the reservoir layer is comprised of a pharmaceutically acceptable pressure-sensitive contact adhesive.

20. The drug reservoir of claim 19, wherein the contact adhesive comprises a continuous hydrophobic polymer phase containing a particulate phase of an inorganic silicate dispersed therein.

21. The drug reservoir of claim 19 wherein the contact adhesive comprises:
    a polymer that is substantially free of functional groups and which, by itself, has cold flow properties selected to provide for effective adhesion to the skin; and
    a porous sorbent material that sorbs a sufficient amount of a polymer-plasticizing component in the drug formulation to maintain the cold flow properties of the adhesive at an acceptable level.

22. A tamsulosin formulation comprising:
    a therapeutically effective amount of tamsulosin, a skin permeation enhancer composition comprising (i) a lipophilic compound having the formula $[RCOO]_nR'$, wherein n is 1 or 2, and R and R' may be the same or different and are $C_1$–$C_{16}$ alkyl optionally substituted with 1 or 2 hydroxyl groups, (ii) an acid having the formula $CH_3(CH_2)_mCOOH$ where m is an integer in the range of 8 to 16; and (iii) a hydrophilic compound selected from the group consisting of diethylene glycol monoethyl ether, diethylene glycol monomethyl ether, propylene glycol, 1,3-butanediol, and butyrolactone optionally substituted with one or two hydroxyl lower alkyl ($C_1$–$C_3$), lower alkoxy ($C_1$–$C_3$) halogen and amino groups.

23. The formulation of claim 22, wherein the lipophilic compound is an ester selected from the group consisting of a compound having the formula $[CH_3(CH_2)_mCO]_nR'$ and a compound having the formula $CH_3(CH_2)_m$—O—CO—$CHR^1R^2$, in which m is an integer in the range of 8 to 16, n is 1 or 2, R' is a lower alkyl ($C_1$–$C_3$) residue that is either unsubstituted or substituted with one or two hydroxyl groups, and $R^1$ and $R^2$ are independently hydrogen, hydroxyl or lower alkyl.

24. The formulation of claim 22, wherein the permeation enhancer composition comprises propylene glycol monolaurate, lauric acid, and 1,3-butanediol.

25. A method for transdermally administering tamsulosin by applying a drug deliver system to the skin or mucosal tissue of an individual, wherein the system comprises:
    a backing layer that is substantially impermeable to tamsulosin; and
    at least one polymeric reservoir layer containing a drug formulation comprised of tamsulosin and a skin permeation enhancer composition effective to facilitate permeation of a therapeutically effective amount of tamsulosin through the skin or mucosal tissue,
    wherein the skin permeation enhancer composition comprises: (i) a lipophilic compound having the formula $[RCOO]_nR'$, wherein n is 1 or 2, and R and R' may be the same or different and are $C_1$–$C_{16}$ alkyl optionally substituted with 1 or 2 hydroxyl groups; (ii) an acid having the formula $CH_3(CH_2)_mCOOH$ where m is an integer in the range of 8 to 16; and (iii) a hydrophilic compound selected from the group consisting of diethylene glycol monoethyl ether, diethylene glycol monomethyl ether, propylene glycol, 1,3-butanediol, and butyrolactone optionally substituted with one or two hydroxyl, lower alkyl ($C_1$–$C_3$), lower alkoxy ($C_1$–$C_3$) halogen and amino groups.

* * * * *